US012636974B2

(12) United States Patent
Hayashi et al.

(10) Patent No.: US 12,636,974 B2
(45) Date of Patent: May 26, 2026

(54) PIEZOELECTRIC SENSOR AND SEAT

(71) Applicant: TOYOTA BOSHOKU KABUSHIKI KAISHA, Aichi (JP)

(72) Inventors: Wataru Hayashi, Aichi (JP); Nobuhiro Moriyama, Tokyo (JP); Tomoyuki Ogawa, Niigata (JP)

(73) Assignee: TOYOTA BOSHOKU KABUSHIKI KAISHA, Aichi (JP)

( * ) Notice: Subject to any disclaimer, the term of this patent is extended or adjusted under 35 U.S.C. 154(b) by 139 days.

(21) Appl. No.: 18/734,161

(22) Filed: Jun. 5, 2024

(65) Prior Publication Data

US 2024/0424957 A1 Dec. 26, 2024

(30) Foreign Application Priority Data

Jun. 21, 2023 (JP) ................................. 2023-102024

(51) Int. Cl.
| | |
|---|---|
| *B60N 2/00* | (2006.01) |
| *A61B 5/11* | (2006.01) |
| *H10N 30/30* | (2023.01) |
| *H10N 30/88* | (2023.01) |

(52) U.S. Cl.
CPC .......... *B60N 2/0022* (2023.08); *A61B 5/1102* (2013.01); *H10N 30/302* (2023.02); *H10N 30/308* (2023.02); *B60N 2210/48* (2023.08); *H10N 30/883* (2023.02)

(58) Field of Classification Search
CPC ........ B64D 11/00155; A47B 2083/025; B60N 2/0022; B60N 2210/48; H10N 30/308; H10N 30/883; H61B 5/1102

USPC ..................... 297/217.3; 73/862.472, 862.68
See application file for complete search history.

(56) References Cited

U.S. PATENT DOCUMENTS

| | | | | |
|---|---|---|---|---|
| 7,598,881 B2 * | 10/2009 | Morgan | ............ | B60R 21/01534 |
| | | | | 340/552 |
| 11,871,674 B1 * | 1/2024 | Smyth | ..................... | G02B 1/115 |
| 2005/0099043 A1 * | 5/2005 | Kim | ....................... | B60N 2/5685 |
| | | | | 297/217.3 |
| 2010/0181871 A1 * | 7/2010 | Daniel | ................. | H10N 30/306 |
| | | | | 73/579 |
| 2015/0008710 A1 * | 1/2015 | Young | .................. | B60N 2/0276 |
| | | | | 297/217.3 |
| 2016/0354027 A1 * | 12/2016 | Benson | .................. | B60N 2/976 |
| 2017/0347961 A1 * | 12/2017 | Perraut | ................ | B60N 2/0022 |
| 2019/0214544 A1 * | 7/2019 | Mori | ...................... | H10N 30/87 |
| 2019/0322524 A1 * | 10/2019 | Lee | ...................... | H10N 30/204 |

(Continued)

FOREIGN PATENT DOCUMENTS

| | | | | |
|---|---|---|---|---|
| JP | 2020-8397 | 1/2020 | | |
| WO | WO-9826716 A1 * | 6/1998 | ............... | A61B 7/00 |
| WO | WO-2018081314 A1 * | 5/2018 | ........... | A61B 5/6802 |

*Primary Examiner* — Jose V Chen
(74) *Attorney, Agent, or Firm* — Greenblum & Bernstein, P.L.C.

(57) ABSTRACT

A piezoelectric sensor includes: a piezoelectric element which is long and which includes a first electrode, a second electrode, and a piezoelectric body interposed between the first and second electrodes; and a laminate film which is long and which surrounds the piezoelectric element. The laminate film includes a wide portion whose length along a shorter side direction of the laminate film is not less than twice a length of the piezoelectric element which length is along a shorter side direction of the piezoelectric element.

7 Claims, 6 Drawing Sheets

(56) References Cited

U.S. PATENT DOCUMENTS

| | | | |
|---|---|---|---|
| 2020/0141794 A1* | 5/2020 | Hiyama | G10K 11/02 |
| 2020/0176668 A1* | 6/2020 | Ogawa | H10N 30/20 |
| 2020/0227621 A1* | 7/2020 | Morishita | H10N 30/708 |
| 2022/0246833 A1* | 8/2022 | Teshigahara | H10N 30/853 |
| 2023/0278477 A1* | 9/2023 | Acome | A47C 7/142 |
| | | | 297/217.3 |
| 2023/0280857 A1* | 9/2023 | Komatsu | H10N 30/302 |
| | | | 345/173 |
| 2023/0386755 A1* | 11/2023 | Tateishi | H10N 30/852 |
| 2023/0413674 A1* | 12/2023 | Miyoshi | H10N 30/50 |
| 2024/0349614 A1* | 10/2024 | Masumoto | H10N 30/708 |
| 2024/0397828 A1* | 11/2024 | Lin | H10N 30/063 |
| 2024/0407266 A1* | 12/2024 | Miyoshi | H10N 30/874 |
| 2025/0268535 A1* | 8/2025 | Nakano | B60N 2/0022 |
| 2025/0311634 A1* | 10/2025 | Nagano | B41J 2/1645 |
| 2025/0339876 A1* | 11/2025 | Imaji | B32B 27/36 |
| 2025/0366720 A1* | 12/2025 | Kitazaki | A61B 5/02042 |

* cited by examiner

PIEZOELECTRIC SENSOR AND SEAT

This Nonprovisional application claims priority under 35 U.S.C. § 119 on Patent Application No. 2023-102024 filed in Japan on Jun. 21, 2023, the entire contents of which are hereby incorporated by reference.

TECHNICAL FIELD

The present disclosure relates to a piezoelectric sensor and a seat.

BACKGROUND ART

Patent Literature 1 discloses a strain gauge including: a plate-shaped base plate; and a sensor element which is stacked on one surface of the plate-shaped base plate and which includes a piezoelectric film. Electrodes are stacked on both surfaces of the piezoelectric film of the sensor element.

CITATION LIST

Patent Literature

[Patent Literature 1]
Japanese Patent Application Publication, Tokukai, No. 2020-8397

SUMMARY OF INVENTION

Technical Problem

The sensor of Patent Literature 1 may be configured such that the widths of the electrodes are increased, for the purpose of improving detection accuracy of the sensor. This, however, results in increase in cost, disadvantageously.

The present disclosure was made in view of the above problem, and has an object to provide: a piezoelectric sensor which can achieve improved sensor detection accuracy while suppressing or reducing increase in cost; and a seat including the piezoelectric sensor.

Solution to Problem

In order to attain the above object, a piezoelectric sensor in accordance with an aspect of the present disclosure includes: a piezoelectric element which is long and which includes a first electrode, a second electrode, and a piezoelectric body interposed between the first electrode and the second electrode; and a film which is long and which surrounds the piezoelectric element. The film includes a wide portion whose length along a shorter side direction of the film is not less than twice a length of the piezoelectric element which length is along a shorter side direction of the piezoelectric element.

Advantageous Effects of Invention

In accordance with an aspect of the present disclosure, it is possible to improve sensor detection accuracy while suppressing or reducing increase in cost.

DESCRIPTION OF EMBODIMENTS

Figure 1:
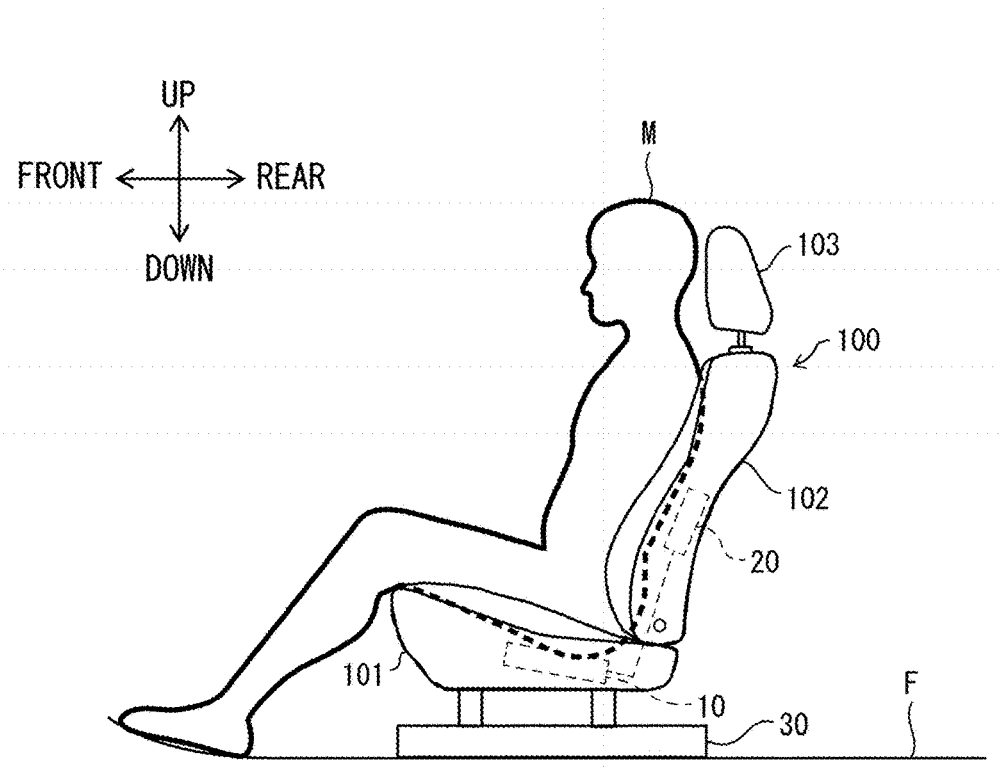
FIG. 1 is a side view schematically illustrating a configuration of a seat including a piezoelectric sensor in accordance with an embodiment of the present disclosure.

The following description will discuss, with reference to FIGS. 1 to 8, a seat 100 including a piezoelectric sensor 10 in accordance with an embodiment of the present disclosure.
[Seat]
FIG. 1 is a side view schematically illustrating a configuration of the seat 100 including the piezoelectric sensor 10. FIG. 1 illustrates a state where a passenger M sits on the seat 100. As shown in FIG. 1, the seat 100 includes a seat cushion 101, a seat back 102, a headrest 103, a piezoelectric sensor 10, a controller 20, and a seat moving device 30. In FIG. 1, the broken line indicates (i) a portion of the back of a passenger M which portion is in contact with the seat back 102 and (ii) a portion of the buttocks of the passenger M which portion is in contact with the seat cushion 101.

The seat 100 is provided in a vehicle, for example. The vehicle is one example of a moving body. The passenger M sits on the seat 100. The seat 100 is a driver's seat, for example. Alternatively, the seat 100 may a passenger's seat or a rear seat. For convenience, an up-down direction and a front-rear direction of the seat 100 are defined as indicated by the arrows in FIG. 1.

The seat cushion 101 is a member for supporting the passenger M's buttocks. The seat cushion 101 includes a cushion frame, a cushion pad covering the cushion frame, and a skin (each of which is not illustrated). The cushion pad is made of a foamed resin such as polyurethane foam.

The seat back 102 is a member for supporting the passenger M's back. The seat back 102 is provided above and backward of the seat cushion 101. The seat back 102 includes a back frame, a back pad covering the back frame, and a skin (each of which is not illustrated). The back pad is made of a foamed resin such as polyurethane foam. The headrest 103 is a member for supporting the passenger M's head, and is provided at an upper end of the seat back 102.

The piezoelectric sensor 10 is disposed inside the seat cushion 101 (details thereof will be described later). The piezoelectric sensor 10 detects ballistocardiology (BCG) B of the passenger M sitting on the seat 100. Note that the piezoelectric sensor 10 may be fixed on an upper surface of a skin of the seat cushion 101.

The piezoelectric sensor 10 is electrically connected to the controller 20. A signal indicative of the ballistocardiology B detected by the piezoelectric sensor 10 is transmitted to the controller 20. The controller 20 measures, on the basis of the signal which is indicative of the ballistocardiology B and which is from the piezoelectric sensor 10, a heart rate of the passenger M sitting on the seat 100.

The controller 20 measures, on the basis of the ballistocardiology B of the passenger M detected by the piezoelectric sensor 10, the heart rate of the passenger M. Then, the controller 20 analyzes a variation in the measured heart rate, so as to derive an R-R Interval (RRI) of the passenger M. The RRI refers to an interval between two successive R waves observed when electrocardiogram of the passenger M is measured.

The seat moving device 30 is a device for supporting the seat cushion 101 and causing the seat 100 to slide in the front-rear direction. The seat moving device 30 includes a pair of right and left slide rails (not illustrated) and a pair of right and left seat lifters (not illustrated) for raising and lowering the seat 100. The seat moving device 30 is disposed on a floor F of the vehicle.

[Configuration of Piezoelectric Sensor]

Figure 2:
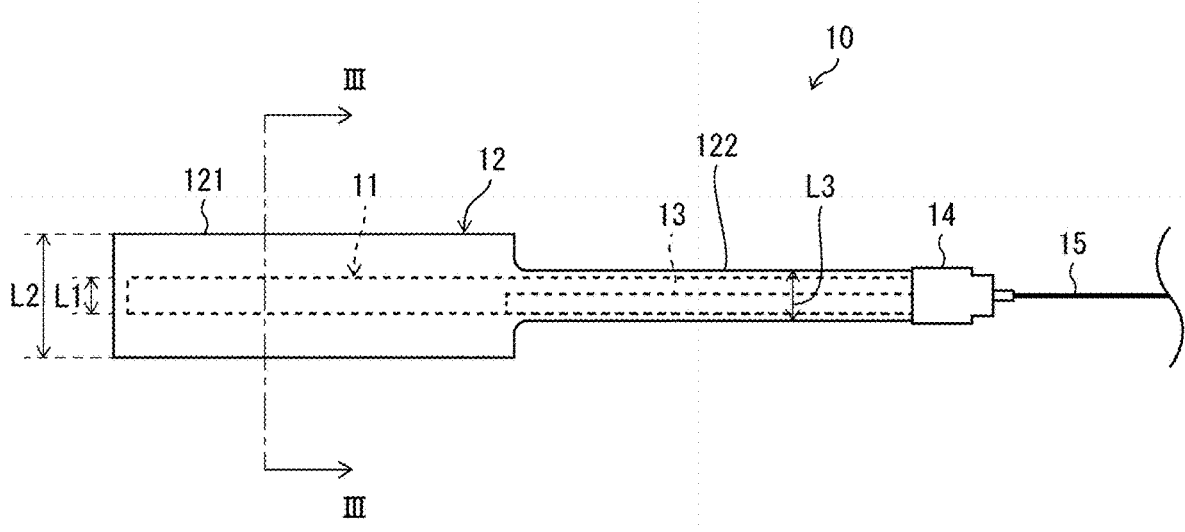
FIG. 2 is a top view illustrating an overall configuration of the piezoelectric sensor shown in FIG. 1.
Figure 3:
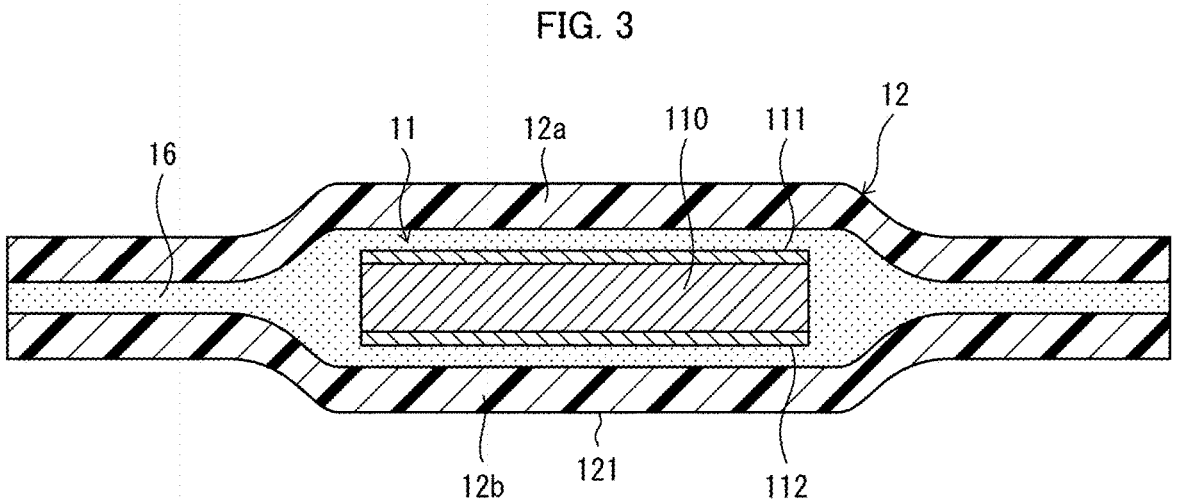
FIG. 3 is a cross-sectional view taken along the line III-III in FIG. 2.

FIG. 2 is a top view illustrating an overall configuration of the piezoelectric sensor 10. FIG. 3 is a cross-sectional view taken along the line III-III in FIG. 2. As shown in FIG. 2, the piezoelectric sensor 10 includes the piezoelectric element 11, a laminate film 12, a flat cable 13, a contractile tube 14, and a shield cable 15. The following will describe a configuration of the piezoelectric sensor 10, referring to FIGS. 2 and 3 as appropriate.

As shown in FIG. 2, the piezoelectric element 11 is a long member. As shown in FIG. 3, the piezoelectric element 11 includes the piezoelectric film 110, a first electrode 111, and a second electrode 112. The piezoelectric film 110 is one example of a piezoelectric body, and is interposed between the first electrode 111 and the second electrode 112.

The piezoelectric film 110 is obtained by, for example, forming a film made of a material having a piezoelectric effect (e.g., poly(vinylidene fluoride) (PVDF)) and cutting the film into a long, belt-like piece. The piezoelectric film 110 outputs voltage according to small contraction, strain, and the like.

Note that the piezoelectric film 110 may be made of, instead of PVDF, trifluoroethylene (TrEF), polylactic acid, polyuric acid, polyamino acid, or the like.

The piezoelectric film 110 has one surface having the first electrode 111 bonded thereto. The first electrode 111 is a thin film member made of silver, for example. The first electrode 111 is a positive electrode, for example. The piezoelectric film 110 has the other surface having the second electrode 112 bonded thereto. The second electrode 112 is a thin film member made of silver, for example. The second electrode 112 is a negative electrode, for example.

The first electrode 111 and the second electrode 112 are connected to the flat cable 13. The flat cable 13 is a thin-plate-like cable made of a plurality of wires which are bundled in parallel and each of which is a copper wire or the like covered with a resin insulator. As compared to the first electrode 111 and the second electrode 112, the flat cable 13 is thicker and more flexible, and therefore is excellent in flexibility (e.g., easily bent). Inside the seat cushion 101, the flat cable 13 is disposed so as to be bent toward the controller 20.

The flat cable 13 is connected to the shield cable 15 via the contractile tube 14. The contractile tube 14 covers outer surfaces of the flat cable 13 and the shield cable 15 so as to fix the flat cable 13 and the shield cable 15.

The shield cable 15 is electrically connected to the controller 20. The shield cable 15 has, on its outer surface, a shield member that cuts off a noise. The shield member is made of a metal foil such as a copper foil.

When a force is applied to the piezoelectric sensor 10, the piezoelectric film 110 is deformed. Along with the deformation, voltage is output from the piezoelectric film 110, so that the first electrode 111 and the second electrode 112 are energized. When the ballistocardiology B of the passenger M sitting on the seat 100 is transmitted to the piezoelectric sensor 10 via the seat cushion 101, voltage is output from the piezoelectric film 110 along with deformation of the piezoelectric film 110.

The voltage output from the piezoelectric film 110 is transmitted to the flat cable 13 and the shield cable 15 via the first electrode 111 and the second electrode 112, and then is input to the controller 20. The controller 20 measures a heart rate of the passenger M on the basis of the detection result of the piezoelectric sensor 10.

The laminate film 12 is one example of a long film covering an outer surface of the piezoelectric element 11, and protects the piezoelectric element 11. The laminate film 12 is made of polyester, for example. A single laminate film 12 is preferably approximately 5 μm to approximately 110 μm in width, for example.

Note that the material of the laminate film 12 is not limited to polyester. Alternatively, the laminate film 12 may be made of polyolefin, a polymethyl methacrylate resin, poly(vinylidene fluoride), or the like. The material of the laminate film 12 may be a mixture of a plurality of kinds of materials. The laminate film 12 may be a stack of a plurality of kinds of materials.

As shown in FIG. 2, the laminate film 12 has a wide portion 121 and a connection portion 122. A length L2 of the wide portion 121 which length L2 is along a shorter side direction of the wide portion 121 is not less than twice and not more than six times a length L1 of the piezoelectric element 11 which length L1 is along a shorter side direction of the piezoelectric element 11. More preferably, the length L2 of the wide portion 121 which length L2 is along the shorter side direction of the wide portion 121 is approximately three times the length L1 of the piezoelectric element 11 which length L1 is along the shorter side direction of the piezoelectric element 11.

With the laminate film 12 configured to include the above-discussed wide portion 121, it is possible to enhance the robustness of the piezoelectric sensor 10 and to secure stable output accuracy of the piezoelectric sensor 10 even for various physiques of passengers M.

Note that the length L1 of the piezoelectric element 11 which length L1 is along the shorter side direction of the piezoelectric element 11 may be approximately 11 mm to approximately 15 mm, for example. More preferably, the length L1 of the piezoelectric element 11 which length L1 is along the shorter side direction of the piezoelectric element 11 may be 13 mm, for example.

The length L2 of the wide portion 121 which length L2 is along the shorter side direction of the wide portion 121 may be approximately 30 mm to approximately 70 mm, more preferably approximately 30 mm to approximately 50 mm.

Still more preferably, the length L2 of the wide portion 121 which length L2 is along the shorter side direction of the wide portion 121 may be 40 mm, for example. In a case where the length L2 of the wide portion 121 which length L2 is along the shorter side direction of the wide portion 121 is approximately 30 mm to approximately 50 mm, the piezo-electric sensor 10 can achieve higher detection accuracy as compared to a case where the length L2 of the wide portion 121 which length L2 is along the shorter side direction of the wide portion 121 is approximately 50 mm to approximately 70 mm (details thereof will be described later).

The connection portion 122 is a portion which is not the wide portion 121. The connection portion 112 extends from one end of the wide portion 121 along the piezoelectric element 11. A length L3 of the connection portion 122 which length L3 is along a shorter side direction of the connection portion 122 is longer, by several millimeters, than the length of the piezoelectric element 11 which length is along the shorter side direction of the piezoelectric element 11. The connection portion 122 has one end provided with the contractile tube 14.

As shown in FIG. 3, the laminate film 12 is made of a single laminate film which is bent so that bent pieces of the piezoelectric element 11 overlap each other and the piezo-electric element 11 is sandwiched therebetween. The lami-nate film 12 is constituted by a first film 12a, which is a portion disposed closer to the first electrode 111 of the piezoelectric element 11, and a second film 12b, which is a portion disposed closer to the second electrode 112 of the piezoelectric element 11. The first film 12a and the second film 12b is made of a single laminate film. Therefore, the first film 12a and the second film 12b have the same thickness. However, even if the first film 12a and the second film 12b is made of a single laminate film, the first film 12a and the second film 12b would naturally have respective different thicknesses, given that a portion serving as the first film 12a and a portion serving as the second film 12b have respective different thicknesses.

Note that the laminate film 12 may be made of two laminate films stacked so that the piezoelectric element 11 is sandwiched therebetween. In this case, the laminate film serving as the first film 12a and the laminate film serving as the second film 12b may have the same thickness or different thicknesses.

The first film 12a and the second film 12b are fixed by an adhesive 16 with the piezoelectric element 11 being sand-wiched between the first film 12a and the second film 12b. Specifically, a surface of the first film 12a which surface is closer to the first electrode 111 and a surface of the second film 12b which surface is closer to the second electrode 112 and faces the surface of the first film 12a are entirely bonded to each other by the adhesive 16. A thickness of the adhesive 16 is preferably approximately 40 μm, for example. Note that the thickness of the adhesive 16 is not limited to 40 μm, and can be changed as appropriate.

Alternatively, in the laminate film 12, the surface of the first film 12a which surface is closer to the first electrode 111 and the surface of the second film 12b which surface is closer to the second electrode 112 and faces the surface of the first film 12a may not be entirely bonded to each other by the adhesive 16. For example, in the laminate film 12, the bonding may be made at least via an area extending several millimeters from an outer periphery of the piezoelectric element 11 as viewed from the top, so that the piezoelectric element 11 can be fixed.

[Arrangement of Piezoelectric Sensor]

Figure 4:
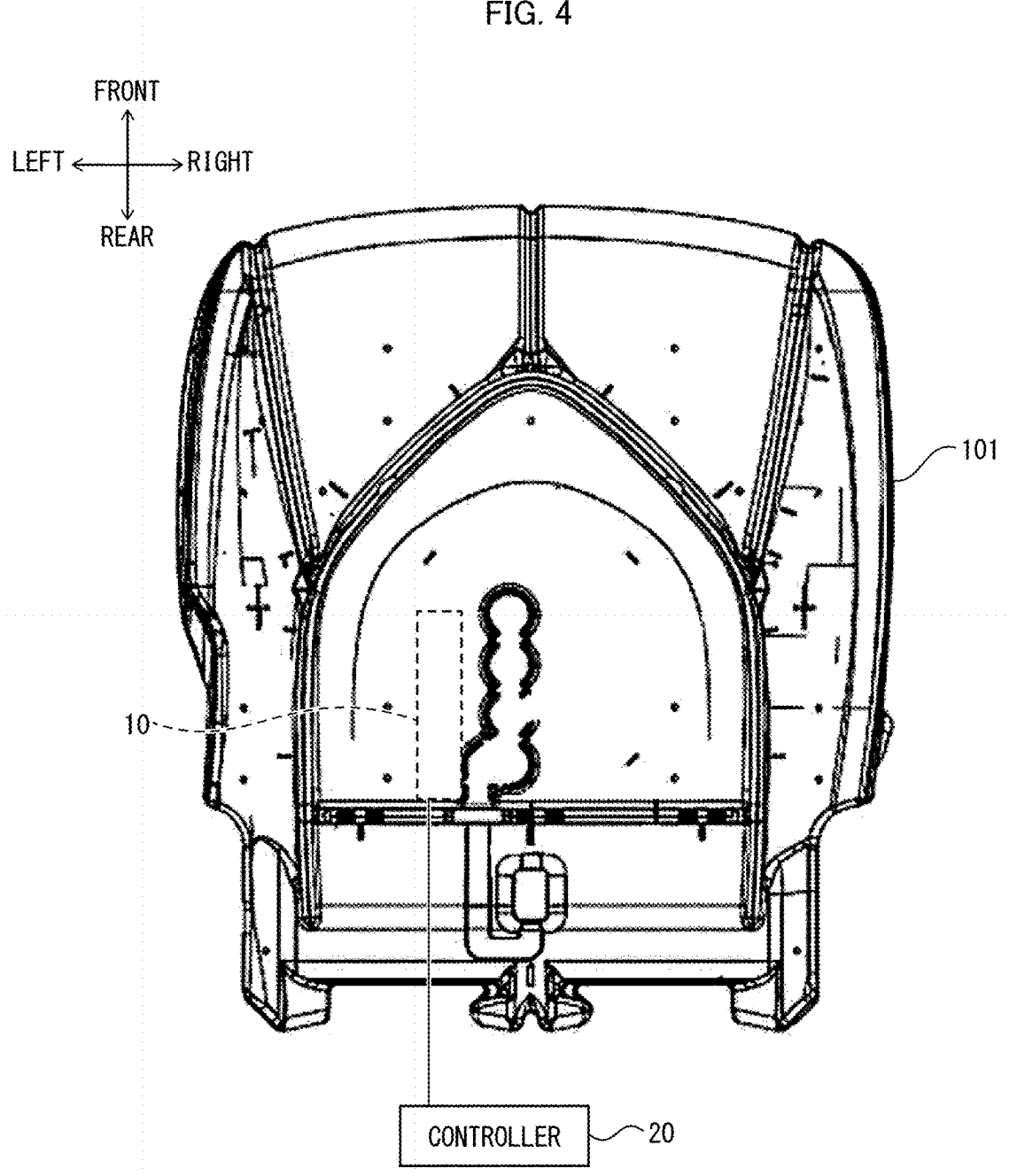
FIG. 4 is a structural diagram schematically illustrating the seat shown in FIG. 1, as viewed from the top.

FIG. 4 is a structural diagram schematically illustrating the seat 100, as viewed from the top. As shown in FIG. 4, the piezoelectric sensor 10 is disposed leftward of a center of the inside of the seat cushion 101 so that the piezoelectric sensor 10 is located closer to the passenger M's heart to improve the sensor detection accuracy. Further, the piezoelectric sensor 10 is long, and is disposed such that a longitudinal direction of the piezoelectric sensor 10 extends along a front-rear direction of the seat cushion 101.

[Effects of Piezoelectric Sensor]

Figures 5, 6:
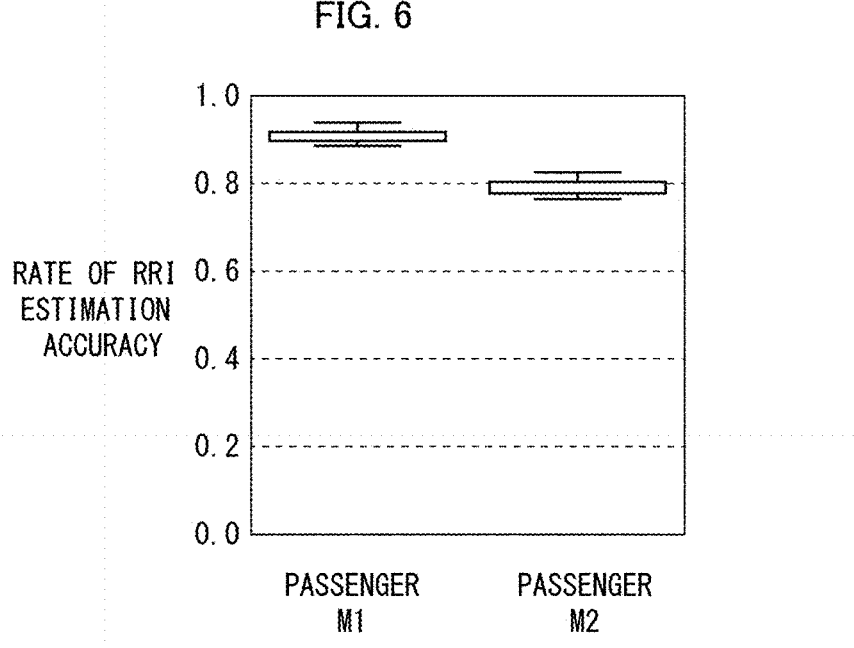
FIG. 5 is a cross-sectional view schematically illustrating the seat shown in FIG. 1, as viewed from the front.
FIG. 6 shows boxplots each illustrating an example of a rate of an RRI estimation accuracy derived from a detection result of passenger's ballistocardiology obtained by the piezoelectric sensor shown in FIG. 1.

FIG. 5 is cross-sectional view schematically illustrating the seat 100, as viewed from the front. In FIG. 5, the passenger M's left thigh is illustrated. As shown in FIG. 5, when the passenger M sits on the seat 100, the ballistocar-diology B of the passenger M is transmitted from the passenger M's thigh to the piezoelectric sensor 10. Note that the piezoelectric sensor 10 also receives vibration noises N transmitted thereto. The vibration noises N include a vibra-tion transmitted from the road while the vehicle is traveling, a vibration of the vehicle's engine, and the like.

FIG. 6 shows boxplots each illustrating a rate of an RRI estimation accuracy derived from a detection result of passenger's ballistocardiology B obtained by the piezoelec-tric sensor 10 in the seat 100 under a dynamic condition that the vehicle was traveling at 80 km per hour. FIG. 6 shows rates of RRI estimation accuracies of two subjects who were to be subjected to detection of ballistocardiology B, that is, the passengers M1 and M2. The passengers M1 and M2 have respective different physiques.

In the example shown in FIG. 6, the rate of the RRI estimation accuracy of the passenger M1 was approximately 0.875 to approximately 0.950. The rate of the RRI estima-tion accuracy of the passenger M2 was approximately 0.750 to approximately 0.825.

Figure 7:
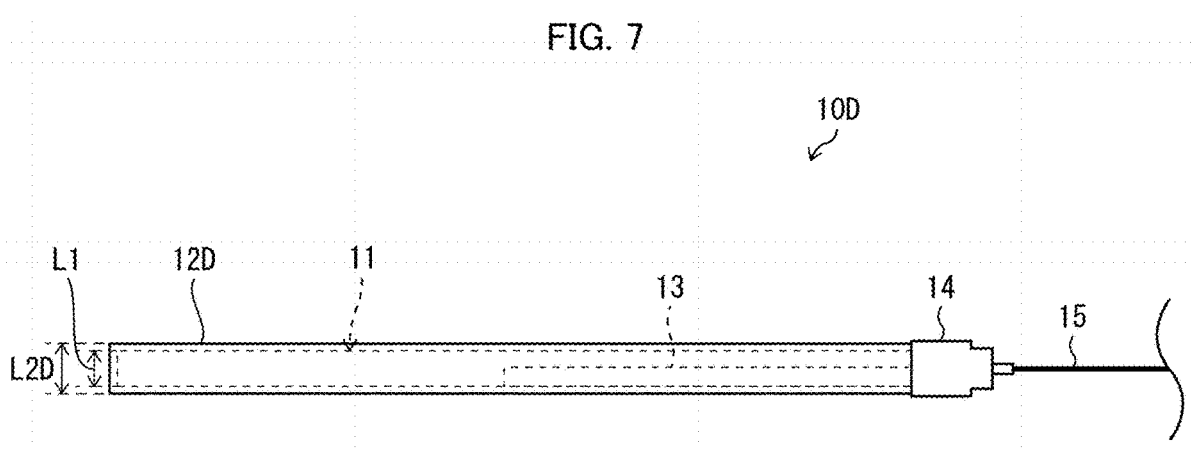
FIG. 7 is a top view illustrating an overall configuration of a piezoelectric sensor in accordance with a comparative example.
Figure 8:
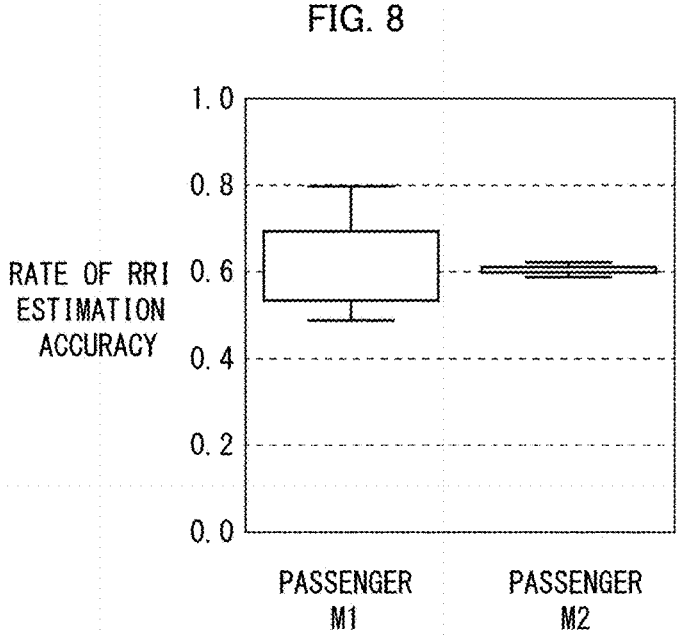
FIG. 8 shows boxplots each illustrating an example of a rate of an RRI estimation accuracy derived from a detection result of passenger's ballistocardiology obtained by the piezoelectric sensor shown in FIG. 7.

FIG. 7 is a top view illustrating an overall configuration of a piezoelectric sensor 10D in accordance with a com-parative example. FIG. 8 shows boxplots each illustrating a rate of an RRI estimation accuracy derived from a detection result of passenger's ballistocardiology B obtained by the piezoelectric sensor 10D shown in FIG. 7. Note that two subjects who were to be subjected to detection of ballisto-cardiology B by the piezoelectric sensor 10D shown in FIG. 7, that is, the passengers M1 and M2 are respectively identical to the passengers M1 and M2 who were to be subjected to detection of the ballistocardiology B by the piezoelectric sensor 10D shown in FIG. 2.

As shown in FIG. 7, unlike the piezoelectric sensor 10 shown in FIG. 1, the piezoelectric sensor 10D does not have a portion corresponding to the wide portion 121 of the piezoelectric sensor 10 shown in FIG. 1. Note that a length L2D of a laminate film 12D which length L2D is along a shorter side direction of the laminate film 12D is longer, by several millimeters, than a length L1 of the piezoelectric element 11 which length L1 is along a shorter side direction of the piezoelectric element 11.

As shown in FIG. 8, the rate of the RRI estimation accuracy of the passenger M1 was approximately 0.500 to approximately 0.800. The rate of the RRI estimation accu-racy of the passenger M2 was approximately 0.575 to approximately 0.6125.

As is clear from FIGS. 6 and 8, the piezoelectric sensor 10, which includes the wide portion 121, was higher in output voltage than the piezoelectric sensor 10D, which does not includes a wide portion. Thus, the piezoelectric sensor 10 could improve the RRI estimation accuracy.

As discussed above, with the piezoelectric sensor 10 in accordance with the present embodiment, it is possible to improve both the RRI estimation accuracies of the passengers M1 and M2. As the RRI estimation accuracy increases, an RRI correct answer rate takes a higher value. That is, by providing the piezoelectric sensor 10 of the present embodiment to the seat 100, it is possible to improve the RRI correct answer rate. The "RRI correct answer rate" herein indicates a percentage that each of differences between RRIs of the passengers M1 and M2 measured for a given period and estimated RRIs of the passengers M1 and M2 shown in FIG. 6 is within 50 msec. There is no particular limitation on the given period.

Effects of Embodiment

With the above-discussed piezoelectric sensor 10 in accordance with the present embodiment, the length L2 of the wide portion 121 of the laminate film 12 which length L2 is along the shorter side direction of the wide portion 121 is set so as to be not less than twice and not more than six times the length L1 of the piezoelectric element 11 which length L1 is along the shorter side direction of the piezoelectric element 11. This can increase an area of a pressure-receiving portion that receives a pressure applied to the piezoelectric sensor 10 from the passenger M sitting on the seat 100. Thus, it is possible to improve the output accuracy of the piezoelectric sensor 10 and to enhance the robustness of the piezoelectric sensor 10.

In particular, with the above configuration, it is not necessary to increase the sizes of the first electrode 111 and the second electrode 112 of the piezoelectric element 11, thereby suppressing or reducing increase in cost. Further, with the piezoelectric sensor 10 in accordance with the present embodiment, it is possible to improve the RRI estimation accuracy.

Furthermore, as shown in FIG. 4, the piezoelectric sensor 10 is disposed at a location leftward of the center of the inside of the seat cushion 101, i.e., at a location closer to the passenger M's heart. Thus, the piezoelectric sensor 10 can detect the ballistocardiology B of the passenger M with high accuracy.

Moreover, as shown in FIG. 4, the piezoelectric sensor 10 is disposed such that the longitudinal direction of the piezoelectric sensor 10 extends along the front-rear direction of the seat cushion 101. This allows the piezoelectric sensor 10 to more easily detect pulses of, e.g., the femoral artery extending along the passenger M's left thigh, thereby improving the accuracy of detection of the ballistocardiology B of the passenger M.

Further, as shown in FIG. 3, the laminate film 12 is configured such that the surface of the first film 12a which surface is closer to the first electrode 111 and the surface of the second film 12b which surface is closer to the second electrode 112 and faces the surface of the first film 12a are entirely fixed to each other by the adhesive 16. This can elongate a penetration length, which is a length it takes for water vapor, corrosive gas, and/or the like outside the piezoelectric sensor 10 to reach the piezoelectric element 11. This can suppress or reduce deterioration of the piezoelectric element 11, thereby elongating the service life of the piezoelectric sensor 10. Furthermore, it is possible to reduce an amount of noises N entering the piezoelectric sensor 10 from the vehicle.

In addition, by making the laminate film 12 of polyester, the laminate film 12 can secure rigidity. Particularly, by increasing an area of a portion of the wide portion 121 of the laminate film 12 in which portion the first film 12a and the second film 12b are bonded to each other, it is possible to improve the bending resistance of the laminate film 12.

Figure 9:
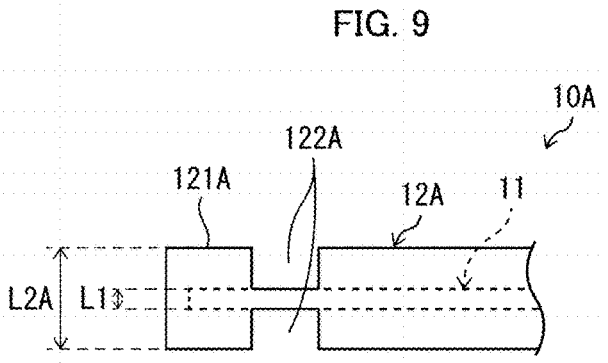
FIG. 9 is a top view illustrating a shape of a wide portion of a film of a piezoelectric sensor in accordance with a first variation of the embodiment.
Figure 10:
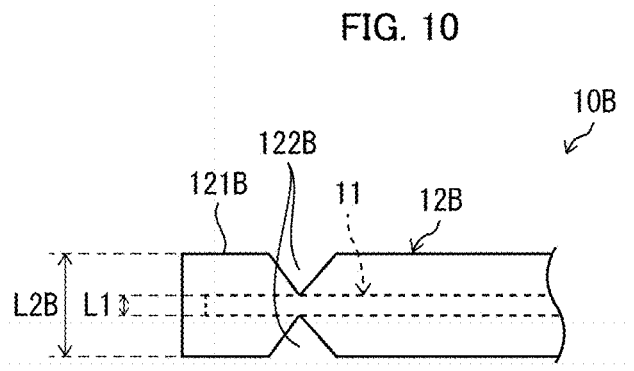
FIG. 10 is a top view illustrating a shape of a wide portion of a film of a piezoelectric sensor in accordance with a second variation of the embodiment.
Figure 11:
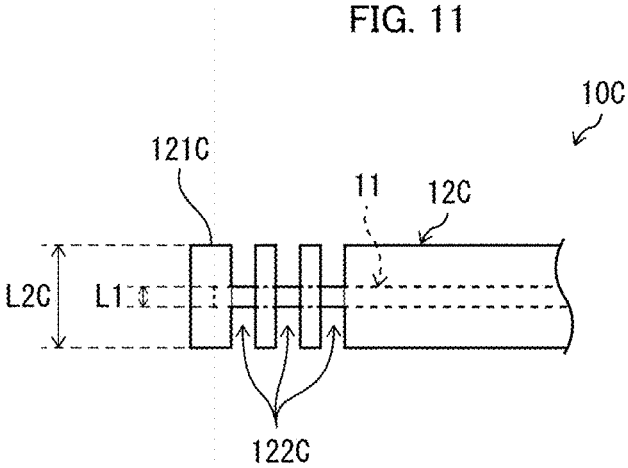
FIG. 11 is a top view illustrating a shape of a wide portion of a film of a piezoelectric sensor in accordance with a third variation of the embodiment.

The following description will discuss, with reference to FIGS. 9 to 11, piezoelectric sensors 10A to 10C in accordance with first to third variations of the above-described embodiment. Note that, for convenience, members having identical functions to those of the foregoing embodiment are given identical reference signs, and their descriptions will be omitted.

[First Variation]

First, the following will describe, with reference to FIG. 9, the piezoelectric sensor 10A in accordance with the first variation. FIG. 9 is a top view illustrating a shape of a wide portion 121A of a laminate film 12A of the piezoelectric sensor 10A in accordance with the first variation. In FIG. 9, a flat cable 13, a contractile tube 14, and a shield cable 15 are not illustrated.

As shown in FIG. 9, the laminate film 12A includes the wide portion 121A. The wide portion 121A has cutouts 122A each having a rectangular shape. That is, the wide portion 121A has a shape obtained by cutting, in an intermediate portion of an area of the wide portion 121A which area is close to one end of the wide portion 121A, a rectangular-shaped portion of the laminate film 12A which portion extends along a shorter side direction of the piezoelectric element 11.

A length L2A of the wide portion 121A which length L2A is along a shorter side direction of the wide portion 121A is approximately four times a length L1 of the piezoelectric element 11 which length L1 is along the shorter side direction of the piezoelectric element 11. Note that the length L2A of the wide portion 121A which length L2A is along the shorter side direction of the wide portion 121A only needs to be not less than twice and not more than six times the length L1 of the piezoelectric element 11 which length L1 is along the shorter side direction of the piezoelectric element 11.

The piezoelectric sensor 10A in accordance with the first variation can also provide similar effects to those of the piezoelectric sensor 10 in accordance with the above-described embodiment. That is, it is possible to improve the output accuracy of the piezoelectric sensor 10A, while enhancing the robustness of the piezoelectric sensor 10A and suppressing or reducing increase in cost.

[Second Variation]

Next, the following will describe, with reference to FIG. 10, the piezoelectric sensor 10B in accordance with the second variation. FIG. 10 is a top view illustrating a shape of a wide portion 121B of a laminate film 12B of the piezoelectric sensor 10B in accordance with the second variation. In FIG. 10, a flat cable 13, a contractile tube 14, and a shield cable 15 are not illustrated.

As shown in FIG. 10, the laminate film 12B has the wide portion 121B. The wide portion 121B has cutouts 122B each having a triangular shape. That is, the wide portion 121B has a shape obtained by cutting, in an intermediate portion of an area of the wide portion 121B which area is close to one end of the wide portion 121B, a triangular-shaped portion of the laminate film 12B which portion extends along a shorter side direction of the piezoelectric element 11.

A length L2B of the wide portion 121B which length L2B is along a shorter side direction of the wide portion 121B is approximately four times a length L1 of the piezoelectric element 11 which length L1 is along the shorter side direction of the piezoelectric element 11. Note that the length L2B of the wide portion 121B which length L2B is along the shorter side direction of the wide portion 121B only needs to be not less than twice and not more than six times the length L1 of the piezoelectric element 11 which length L1 is along the shorter side direction of the piezoelectric element 11.

The piezoelectric sensor 10B in accordance with the second variation can also provide similar effects to those of the piezoelectric sensor 10 in accordance with the above-described embodiment. That is, it is possible to improve the output accuracy of the piezoelectric sensor 10B, while enhancing the robustness of the piezoelectric sensor 10B and suppressing or reducing increase in cost.

[Third Variation]

Next, the following will describe, with reference to FIG. 11, the piezoelectric sensor 10C in accordance with the third variation. FIG. 11 is a top view illustrating a shape of a wide portion 121C of a laminate film 12C of the piezoelectric sensor 10C in accordance with the third variation. In FIG. 11, a flat cable 13, a contractile tube 14, and a shield cable 15 are not illustrated.

As shown in FIG. 11, the laminate film 12C includes the wide portion 121C. The wide portion 121C has a plurality of cutouts 122C each having a rectangular shape. That is, the wide portion 121C has a bellows shape obtained by cutting, in an intermediate portion of an area of the wide portion 121C which area is close to one end of the wide portion 121C, rectangular-shaped portions of the laminate film 12C which portions extend along a shorter side direction of the piezoelectric element 11.

A length L2C of the wide portion 121C which length L2C is along a shorter side direction of the wide portion 121C is approximately four times a length L1 of the piezoelectric element 11 which length L1 is along the shorter side direction of the piezoelectric element 11. Note that the length L2C of the wide portion 121C which length L2C is along the shorter side direction of the wide portion 121C only needs to be not less than twice and not more than six times the length L1 of the piezoelectric element 11 which length L1 is along the shorter side direction of the piezoelectric element 11.

The piezoelectric sensor 10C in accordance with the third variation can also provide similar effects to those of the piezoelectric sensor 10 in accordance with the above-described embodiment. That is, it is possible to improve the output accuracy of the piezoelectric sensor 10C, while enhancing the robustness of the piezoelectric sensor 10C and suppressing or reducing increase in cost.

OTHER EMBODIMENTS

In the foregoing embodiment, the seat 100 is provided in the vehicle, which is one example of the moving body. However, this is not limitative. For example, the seat 100 may be provided in a train, an aircraft, a ship, or the like.

In the piezoelectric sensor 10 in accordance with the foregoing embodiment, the wide portion 121 of the laminate film 12 has a rectangular shape as shown in FIG. 2. However, this is not limitative. Alternatively, for example, the laminate film 12 may have an oval shape or a polygonal shape.

In the foregoing embodiment, the piezoelectric sensor 10 is disposed leftward of the center of the inside of the seat cushion 101. However, this is not limitative. Alternatively, for example, the piezoelectric sensor 10 may be disposed in the center of the inside of the seat cushion 101 or rightward of the center of the inside of the seat cushion 101. Further alternatively, the piezoelectric sensor 10 may be disposed inside the seat back 102.

In the foregoing embodiment, the controller 20 measures the passenger M's heart rate on the basis of the detection result of the single piezoelectric sensor 10. However, this is not limitative. Alternatively, the controller 20 may measure the passenger M's heart rate on the basis of detection results of a plurality of piezoelectric sensors 10 included in the vehicle.

In the foregoing embodiment, the seat 100 includes the seat cushion 101, the seat back 102, and the headrest 103. However, this is not limitative. The seat 100 may not include the seat back 102 or the headrest 103, and may include only the seat cushion 101. Further, the seat 100 encompasses a bed, a mat, and the like.

The present disclosure is not limited to the embodiments above, but can be altered by a skilled person in the art within the scope of the claims. The present disclosure also encompasses, in its technical scope, any embodiment derived by combining technical means disclosed in differing embodiments as appropriate.

REFERENCE SIGNS LIST 10, 10A, 10B, 10C: piezoelectric sensor
11: piezoelectric element
12, 12A, 12B, 12C: laminate film
16: adhesive
20: controller
100: seat
110: piezoelectric film
111: first electrode
112: second electrode
121, 121A, 121B, 121C: wide portion
B: ballistocardiology
M, M1, M2: passenger

The invention claimed is:

1. A piezoelectric sensor comprising:
a piezoelectric element extending in a longitudinal direction, the piezoelectric element including a first electrode, a second electrode, and a piezoelectric body interposed between the first electrode and the second electrode; and
a film extending in the longitudinal direction, and surrounding the piezoelectric element,
the film including a wide portion having a length in a width direction, which is a direction perpendicular to a longitudinal direction of the film, the length of the wide portion being at least twice as large as a width of the piezoelectric element, the width being measured in a direction perpendicular to a longitudinal direction of the piezoelectric element.

2. The piezoelectric sensor according to claim 1, wherein:
the length of the wide portion which length is along the shorter side direction of the film is not more than six time the length of the piezoelectric element which length is along the shorter side direction of the piezoelectric element.

3. The piezoelectric sensor according to claim 1, wherein:
the wide portion has at least one cutout.

4. The piezoelectric sensor according to claim 1, wherein:
the film includes
a first film disposed closer to the first electrode of the piezoelectric element and
a second film disposed closer to the second electrode of the piezoelectric element; and
a surface of the first film which surface is closer to the first electrode and a surface of the second film which surface is closer to the second electrode are entirely fixed to each other by an adhesive.

5. A seat comprising:
a piezoelectric sensor recited in claim 1,
the seat being provided to a moving body,
the piezoelectric sensor being provided to the seat so as to detect ballistocardiology of a passenger who sits on the seat.

6. The seat according to claim 5, further comprising:
a seat cushion supporting buttocks of the passenger,
the piezoelectric sensor being disposed leftward of a center of an inside of the seat cushion.

7. The seat according to claim 6, wherein:
the piezoelectric sensor extends in the longitudinal direction, and is disposed such that the longitudinal direction extends along a front-rear direction of the seat cushion.

\* \* \* \* \*